United States Patent [19]

Callender, Jr.

[11] 3,958,567

[45] May 25, 1976

[54] DEROTATION BRACE FOR TIBIA DEFORMITIES

[76] Inventor: George R. Callender, Jr., 4701 MacCorkle Ave., SE., Charleston, W. Va. 25304

[22] Filed: Apr. 29, 1975

[21] Appl. No.: 572,923

[52] U.S. Cl............................................... 128/80 R
[51] Int. Cl.² ............................................ A61F 3/00
[58] Field of Search ............... 128/80 R, 80 A, 80 B, 128/80 E, 80 J, 83, 87

[56] References Cited
UNITED STATES PATENTS

| 9,472 | 12/1852 | Hussey | 128/80 A |
|---|---|---|---|
| 114,669 | 5/1871 | Grant | 128/80 J |
| 2,410,560 | 11/1946 | Witte | 128/80 F |
| 3,086,522 | 4/1963 | Frohmader | 128/80 J |
| 3,171,407 | 3/1965 | Rogers | 128/80 J |
| 3,304,937 | 2/1967 | Callender, Jr. | 128/80 R |
| 3,805,773 | 4/1974 | Sichau | 128/80 E |

FOREIGN PATENTS OR APPLICATIONS

| 1,126,942 | 12/1956 | France | 128/80 A |

*Primary Examiner*—John D. Yasko
*Attorney, Agent, or Firm*—Clarence A. O'Brien; Harvey B. Jacobson

[57] ABSTRACT

An upstanding rigid vertical brace bar constructed so as to be adjustable in length is provided and includes upper and lower end oppositely directed generally horizontal terminal end portions. The brace bar is adapted to extend downwardly behind the calf portion of the leg of the wearer and the upper horizontally directed terminal end portion is adapted to underlie the thigh portion of the leg of the wearer, the brace bar and upper terminal end portion each including an adjustable length strap member for clamping about the associated leg portion of the wearer. The lower horizontally directed terminal end portion supports a shoe cradle therefrom for adjustable angular displacement about an upstanding axis and releasable securement in adjusted rotated position. The shoe cradle is constructed so as to snugly receive and embrace a foot worn shoe of the user and the cradle also includes strap structure for strappingly securing the shoe of the wearer in the cradle. Further, the juncture between the upper end of the brace bar and the adjacent end of the upper horizontal terminal end portion includes a transverse enlargement whereby the posterior portion of the knee of the user and adjacent leg surfaces may be cushioned.

3 Claims, 5 Drawing Figures

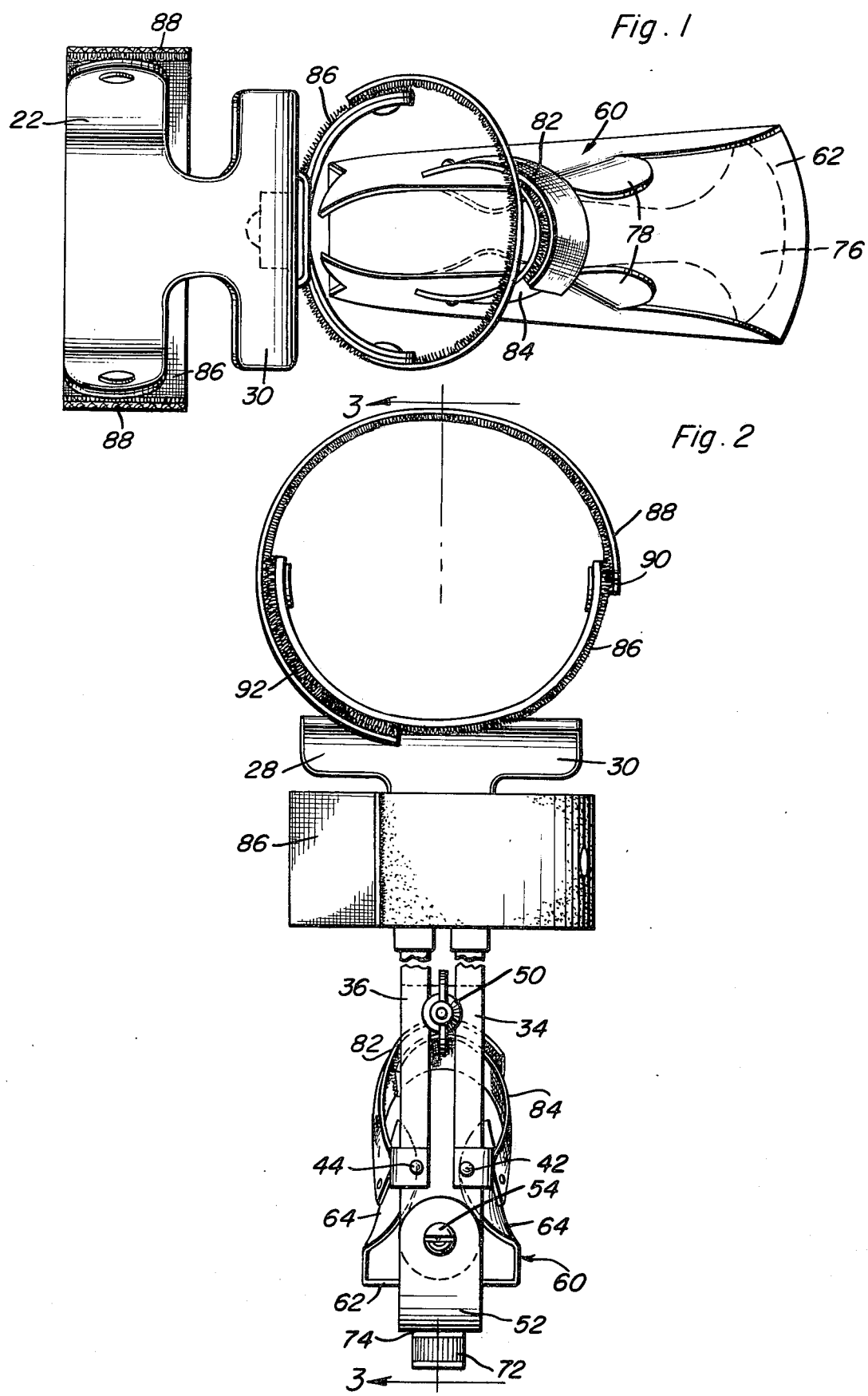

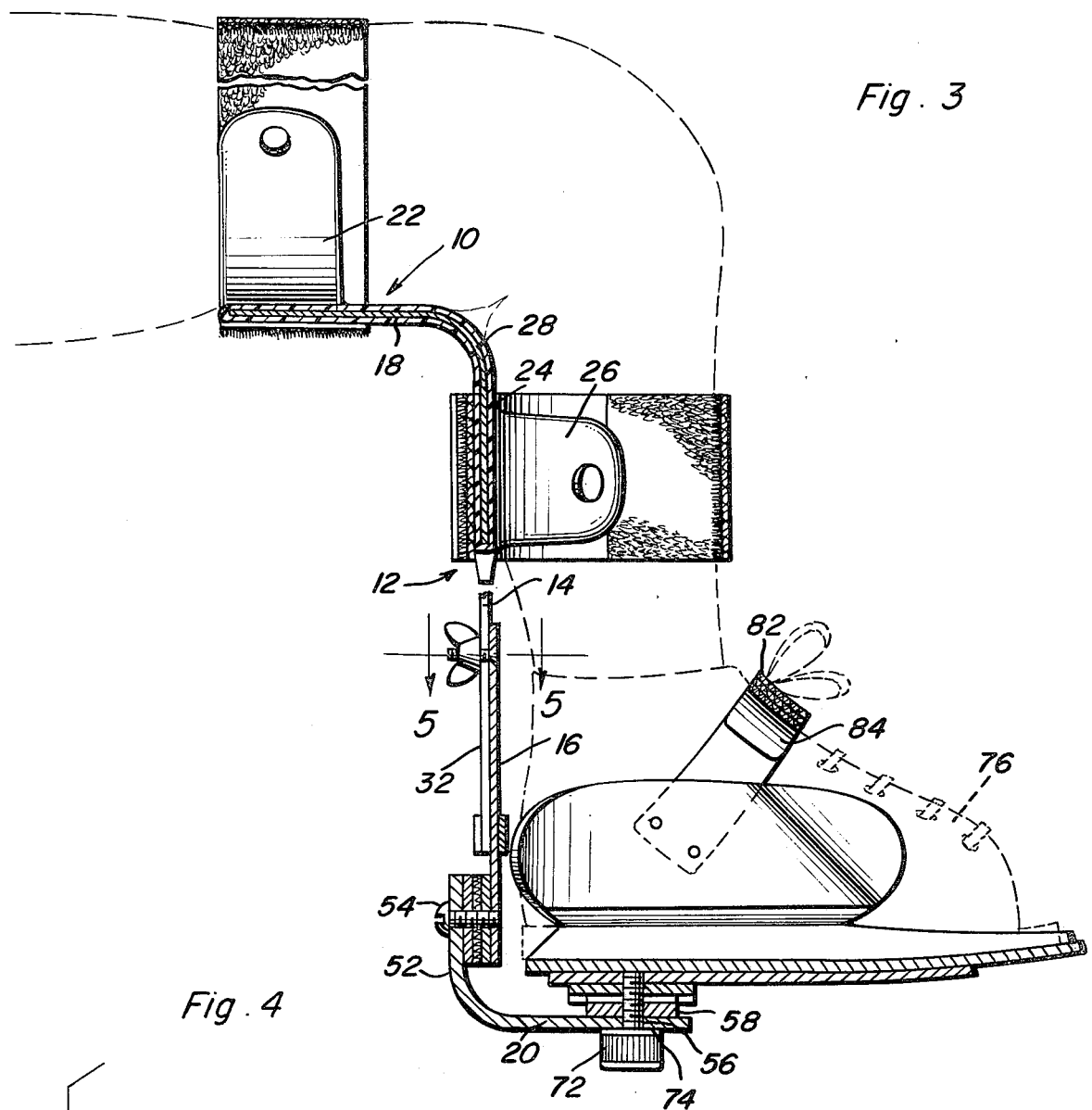
Fig. 3
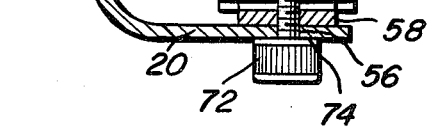
Fig. 4
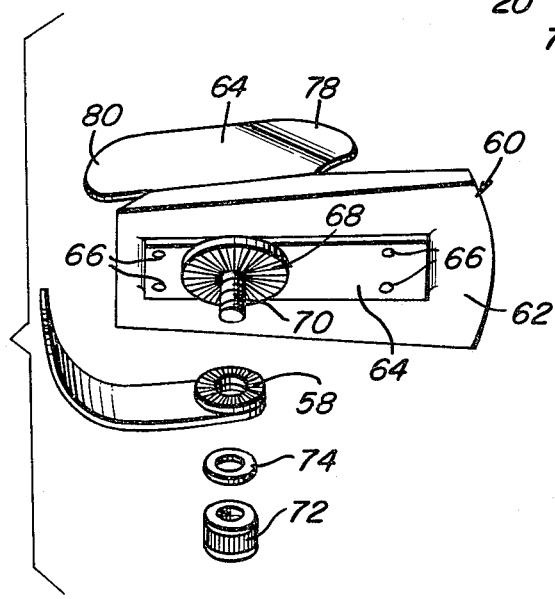
Fig. 5
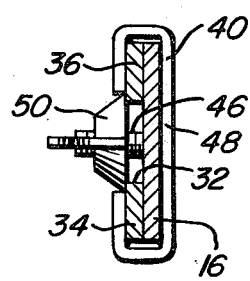

DEROTATION BRACE FOR TIBIA DEFORMITIES

This invention comprises an improvement over the derotation brace disclosed in my prior U.S. Pat. No. 3,304,937, dated Feb. 21, 1967.

BACKGROUND OF THE INVENTION

The derotation brace disclosed in my above noted prior patent was not specifically designed to support a user's foot while enclosed within a conventional shoe and therefore required specially constructed partial shoes and it was necessary to design a special partial shoe for substantially all users in order to provide sufficient support for the metatarsal. In addition, my previously patented derotation brace was not readily adaptable to persons having calf portions of different lengths and sufficient protection was not provided for the popliteal fossa.

The derotation brace of the instant invention has been engineered to provide all of the additional protection feature found to be beneficial after considerable usage and testing of my previously patented derotation brace.

BRIEF DESCRIPTION OF THE INVENTION

The derotation brace of the instant invention is constructed in a manner whereby it is adapted for use by persons wearing their own shoes and whereby sufficient support for the user's metatarsal is afforded. Further, improved strap-type fastening means are provided for anchoring the brace to the leg of the user and the brace is readily adjustable so as to compensate for lower leg calf portions of different lengths. Further, the brace of the instant invention provides ample protection for the popliteal fossa.

The main object of this invention is to provide an improved derotation brace for tibia deformities and which may be readily adapted to persons having calf leg portions of different lengths.

Another important object of this invention is to provide a derotation brace constructed in a manner whereby the foot of the leg of the user to which the brace is secured may be enclosed within a conventional shoe for normal protection of the foot associated with the wearing of a shoe.

Yet another object of this invention is to provide a derotation brace including structure for adequately cushioning and protecting the popliteal fossa of the user.

A final object of this invention to be specifically enumerated herein is to provide a derotation brace in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a top plan view of the brace of the instant invention;

FIG. 2 is a rear elevational view of the brace;

FIG. 3 is a vertical sectional view taken substantially upon the plane indicated by the section line 3—3 of FIG. 2 and with an associated leg illustrated in phantom lines;

FIG. 4 is an exploded perspective view of the lower shoe supporting portion of the brace; and FIG. 5 is an enlarged horizontal sectional view taken substantially upon the plane indicated by the section line 5—5 of FIG. 3.

DETAILED DESCRIPTION OF THE INVENTION

Referring now more specifically to the drawings, the numeral 10 generally designates the brace of the instant invention. The brace 10 includes an upstanding elongated brace bar referred to in general by the reference numeral 12 including strap type upper and lower end portions 14 and 16. The upper end portion 14 terminates in an integral rearwardly and horizontally directed upper terminal strap end portion 18 and the lower end portion 16 of the brace bar 12 includes a forwardly directed horizontal terminal end portion 20.

Formed integrally with the rear end of the upper terminal end portion 18 is an upwardly opening U-shaped cradle 22 and the upper portion 24 of the upper end portion 14 includes an integral forwardly opening U-shaped cradle 26. The entire upper end portion 14, including the upper terminal end portion 18 and the cradles 22 and 26 disposed above the lower portion of the cradle 26 is coated with a resilient coating 28 and the juncture between the upper portion 24 and the upper terminal end portion 18 defines a transversely widened generally quarter cylindrical horizontally disposed shield 30 projecting outwardly from opposite sides of the strap portions 14 and 18 also covered in its entirety by the coating 28.

The lower extremity of the upper end portion 14 is centrally slotted as at 32 and the slot 32 opens downwardly through the lower extremity of the upper end portion 14 thereby defining a pair of parallel arms 34 and 36.

A C-shaped guide 40 embraces and interconnects the lower ends of the legs or arms 34 and 36, the clip 40 being secured to the legs 34 and 36 by means of suitable fasteners 42 and 44.

The upper end of the lower end portion 16 includes a centrally disposed rearwardly projecting threaded shank portion 46 which is slidably received in the slot 32 defined between the legs 34 and 36 and the upper end of the lower end portion 16 is received between the rear surface of the forward cross member 48 of the clip 40 and the forward surfaces of the legs 34 and 36, a threaded wing nut 50 being threadedly engaged with the shank portion 46 and tightened thereon so as to secure the upper and lower portions of the lower and upper end portions 16 and 14 in adjusted overlapped positions.

The free lower end of the lower end portion 16 has an upwardly directed integral rear mounting flange portion 52 of the lower terminal end portion 20 secured thereto by means of a releasable threaded fastener 54 and the forward portion of the lower terminal end portion 20 is apertured as at 56 and has a radially serrated washer 58 secured to its upper surface.

A generally channel-shaped shoe cradle assembly referred to in general by the reference numeral 60 is provided and includes a longitudinally extending lower plate 62 including upwardly directed contoured opposite side flanges 64. The lower plate 62 is strengthened and reinforced by an underlying longitudinal bar 65 secured thereto by means of fasteners 66 and the bar 65 includes a radially serrated washer or disc 68 secured to its undersurface and including a downwardly projecting centrally disposed threaded stud 70.

The cradle assembly 60 is positionable over the washer 58 with the stud 70 projecting therethrough as well as the bore 56 and a threaded nut 72 and washer 74 are secured on the lower end of the stud 70 projecting downwardly through the bore 56. In this manner, the cradle assembly 60 may be secured in adjusted rotated position about an upstanding axis defined by the stud 70.

The lower portions of the flanges 64 extend substantially the full length of the cradle assembly 60 and are slightly inwardly and upwardly inclined so as to clamp over the opposite side sole portions of the shoe 76 of the wearer and the upper portions of the flanges 64 are somewhat deformable so that the forward end portions 78 thereof and the rear end portions 80 thereof may be deflected inwardly over the forward opposite side portions of the shoe 76 and inwardly behind the outer rear heel portions of the shoe 76. The opposite side flanges 78 have coacting Velcro strips 82 and 84 secured thereto whereby the Velcro strips 82 and 84 may be fastened to secure the shoe 76 within the cradle assembly 60 and each of the cradles 22 and 26 has a Velcro strip 86 secured to its outer convex surface. In addition, each of the cradles 22 and 26 includes a second Velcro strip 88 secured at one end to the corresponding cradle as at 90 and the other end of each second Velcro strip 88 may be adjustably lapped over and secured to the corresponding Velcro strip 86 as at 92 in order to tightly clamp the lower calf portion and upper thigh portion of the user's leg in the cradles 26 and 22.

The fastener 54 serves both as a clamp type fastener and a pivot fastener and is secured through the rear mounting flange portion 52 as well as the lower end of the lower end portion 16 and serrated washers corresponding to washers 58 and 68 carried by the portions 52 and 16, whereby the end portion 20 and cradle assembly 60 may be secured in adjusted rotated positions, relative to the portion 16, about the pivot axis defined by the fastener 54.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A derotation leg brace for treatment of internal torsion or external torsion of the tibia bone comprising a rigid strap-type vertical brace bar having upper and lower end portions as well as front and rear sides and adapted to extend along the posterior of the calf portion of the leg of a user, said upper end portion including an integral rearwardly directed angulated strap-type upper terminal end portion adapted to underlie the underside of the thigh portion of said leg with the knee of the user bent to conform to the relative angulation of said brace bar and upper terminal end portion, said upper terminal end portion being joined to said upper end portion by means of a trasversely extending generally quarter cylindrical connecting portion integral with said upper end portion and terminal end portion, projecting outwardly of the opposite sides thereof and adapted to cushion and protect the popliteal fossa of the user, said upper terminal end portion and said upper end portion of said brace bar including transverse integral upwardly and forwardly opening rigid U-shaped leg cradles, respectively, adapted to cradle the thigh and calf portions, respectively, of the user, each of said cradles including adjustable strap means operatively associated therewith for clamping the corresponding leg portion in the ssociated cradle, the lower end portion of said brace bar including a forwardly directed angulated lower terminal end portion, an upwardly opening shoe cradle for cradling the shoe of the user of said brace supported from a forward portion of said lower terminal end portion for adjustable angular displacement of said shoe cradle relative to said lower terminal end portion about an upstanding axis fixed relative to said lower terminal end portion and generally paralleling and spaced forward of said brace bar, said shoe cradle including a lower plate for resting the sole of an associated shoe thereon and means for substantially stationarily anchoring a shoe therein with the sole of the shoe abutted against the lower plate, said upper and lower end portions being slidingly overlappingly engaged with each other for limited guided relative longitudinal extension and retraction, means connected between said upper and lower end portions releasably retaining the latter in infinite relative adjusted positions within the limits thereof, means supporting said lower terminal end portion from said lower end portion of said brace bar for adjustable swinging about a front to rear extending axis spaced above said lower plate and said lower terminal end portion and stationary relative to the latter, means connected between said lower end portion of said brace bar and said lower terminal end portion releasably retaining the latter in adjusted rotated position relative to said lower end portion of said brace bar.

2. The combination of claim 1 wherein said shoe cradle includes opposite side upstanding longitudinal side flanges, extending along opposite sides of said lower plate, the rear ends of said side flanges curving inwardly toward each other for embracing the heel of the upper of said shoe and the forward ends of said flanges having their upper portions curved inwardly and downwardly for embracing the forward instep portion of the shoe upper.

3. The combination of claim 2 wherein the longitudinal mid-portions of said flanges have the lower ends of a pair of opposite side forwardly and upwardly inclined flexible strap members anchored thereto, the upper ends of said strap members including coacting means for releasably securing said upper ends to each other in adjusted overlapped positions.

* * * * *